(12) United States Patent
Peckermann et al.

(10) Patent No.: US 10,759,902 B2
(45) Date of Patent: Sep. 1, 2020

(54) PROCESS FOR THE PRODUCTION OF POLYOXYMETHYLENE BLOCK COPOLYMERS

(71) Applicant: Covestro Deutschland AG, Leverkusen (DE)

(72) Inventors: Ilja Peckermann, Cologne (DE); Aurel Wolf, Wülfrath (DE); Jens Langanke, Mechernich (DE); Christoph Gürtler, Cologne (DE); Jörg Hofmann, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 126 days.

(21) Appl. No.: 16/120,566

(22) Filed: Sep. 4, 2018

(65) Prior Publication Data

US 2018/0371159 A1    Dec. 27, 2018

Related U.S. Application Data

(62) Division of application No. 15/129,209, filed as application No. PCT/EP2015/057209 on Apr. 1, 2015, now Pat. No. 10,093,772.

(30) Foreign Application Priority Data

Apr. 7, 2014 (EP) ..................... 14163744
Feb. 23, 2015 (EP) ..................... 15156102

(51) Int. Cl.
C08G 64/34 (2006.01)
C08G 2/38 (2006.01)
C08G 64/02 (2006.01)
C08G 18/44 (2006.01)
C08G 18/48 (2006.01)
C08G 18/56 (2006.01)
C08G 64/18 (2006.01)
A61K 8/86 (2006.01)
A61Q 19/00 (2006.01)
C08G 18/08 (2006.01)
C08G 18/72 (2006.01)
C08G 65/26 (2006.01)
C09K 8/035 (2006.01)
C10L 1/238 (2006.01)
C10M 149/20 (2006.01)
C08G 101/00 (2006.01)

(52) U.S. Cl.
CPC ........... *C08G 64/0208* (2013.01); *A61K 8/86* (2013.01); *A61Q 19/00* (2013.01); *C08G 2/38* (2013.01); *C08G 18/14* (2013.01); *C08G 18/44* (2013.01); *C08G 18/4866* (2013.01); *C08G 18/56* (2013.01); *C08G 18/72* (2013.01); *C08G 64/183* (2013.01); *C08G 64/34* (2013.01); *C08G 65/2603* (2013.01); *C08G 65/2663* (2013.01); *C09K 8/035* (2013.01); *C10L 1/2381* (2013.01); *C10M 149/20* (2013.01); *A61K 2800/10* (2013.01); *C08G 2101/00* (2013.01); *C08G 2101/0008* (2013.01); *C08G 2101/0025* (2013.01); *C08G 2650/58* (2013.01); *C10L 2200/0259* (2013.01); *C10M 2217/045* (2013.01)

(58) Field of Classification Search
CPC ................................................. C08G 64/0208
USPC ............................................................. 528/230
See application file for complete search history.

(56) References Cited

U.S. PATENT DOCUMENTS

| | | |
|---|---|---|
| 3,404,109 A | 10/1968 | Milgrom |
| 3,436,375 A | 4/1969 | McAndrew |
| 3,575,930 A | 4/1971 | Dinbergs |
| 3,754,053 A | 8/1973 | Kray et al. |
| 3,829,505 A | 8/1974 | Herold |
| 3,941,849 A | 3/1976 | Herold |
| 4,355,188 A | 10/1982 | Herold et al. |
| 4,380,620 A | 4/1983 | Matsuzaki et al. |
| 4,721,818 A | 1/1988 | Harper et al. |
| 4,877,906 A | 10/1989 | Harper |
| 4,987,271 A | 1/1991 | Watabe et al. |
| 5,099,075 A | 3/1992 | Katz et al. |
| 5,158,922 A | 10/1992 | Hinney et al. |
| 5,391,722 A | 2/1995 | Chandalia et al. |
| 5,470,813 A | 11/1995 | Le-Khac |
| 5,482,908 A | 1/1996 | Le-Khac |
| 5,637,673 A | 6/1997 | Le-Khac |

(Continued)

FOREIGN PATENT DOCUMENTS

| | | |
|---|---|---|
| EP | 0385619 A2 | 9/1990 |
| EP | 0406440 A1 | 1/1991 |

(Continued)

OTHER PUBLICATIONS

Haubs et al.; Ullmann's Encyclopedia of Industrial Chemistry; Polyoxymethylenes; pp. 1-16; 2012 Wiley-VCH Verlag GmbH & Co.; Frankfurt, Germany.

(Continued)

Primary Examiner — Duc Truong
(74) Attorney, Agent, or Firm — N. Denise Brown

(57) ABSTRACT

The invention relates to a process for producing polyoxymethylene block copolymers, comprising the step of activating the DMC catalyst in the presence of an OH-terminated polymeric formaldehyde starter compound by means of a defined amount of alkylene oxide, optionally followed by polymerization with alkylene oxides, if necessary in the presence of other comonomers. The invention further relates to polyoxymethylene block copolymers that can be obtained by means of such a process and to the use of these for producing polyurethane polymers.

10 Claims, No Drawings

(56) References Cited

U.S. PATENT DOCUMENTS

| | | | |
|---|---|---|---|
| 5,714,428 | A | 2/1998 | Le-Khac |
| 5,789,626 | A | 8/1998 | Le-Khac |
| 6,018,017 | A | 1/2000 | Le-Khac |
| 7,001,959 | B2 | 2/2006 | Mück et al. |
| 7,008,900 | B1 | 3/2006 | Hofmann et al. |
| 7,538,162 | B2 | 5/2009 | Haider et al. |
| 9,790,328 | B2 | 10/2017 | Mueller et al. |
| 2002/0016395 | A1 | 2/2002 | Niino et al. |
| 2006/0205915 | A1 | 9/2006 | Groer et al. |

FOREIGN PATENT DOCUMENTS

| | | |
|---|---|---|
| GB | 807589 | 1/1959 |
| JP | 03263454 | 11/1991 |
| JP | 04306215 | 10/1992 |
| JP | 2928823 | 8/1999 |
| JP | 2007211082 | 8/2007 |
| WO | 2004096746 A1 | 11/2004 |
| WO | 2012091968 A1 | 7/2012 |

OTHER PUBLICATIONS

Franz et al.; Ullmann's Encyclopedia of Industrial Chemistry; Formaldehyde; pp. 1-34; 2016 Wiley-VCH Verlag GmbH & Co.; Ludwigshafen, Germany.

Matsuzaki et al.; "New Polyacetal Process from Formaldehyde Polymerization in the Presence of a Chain Transfer Agent"; Bull. Chem. Soc. Jpn.; vol. 67, No. 9; pp. 2560-2566; 1994; The Chemical Society of Japan.

Ionescu, Mihail; Chemistry and Technology of Polyols for Polyurethanes; Rapra Technology Limited; p. 123; Shawbury, Shrewsbury, Shropshire, SY4 4NR, United Kingdom.

PROCESS FOR THE PRODUCTION OF POLYOXYMETHYLENE BLOCK COPOLYMERS

CROSS-REFERENCE TO RELATED APPLICATIONS

This application is a Divisional Application of U.S. application Ser. No. 15/129,209 filed on Sep. 26, 2016 now U.S. Pat. No. 10,093,772 which is a National Phase Application of PCT/EP2015/057209, filed Apr. 1, 2015, which claims priority to European Application No. 14163744.7 filed Apr. 7, 2014 and European Application No. 15156102.4 filed Feb. 23, 2015, each of which being incorporated herein by reference.

FIELD

The present invention describes a process for preparing polyoxymethylene block copolymers. It further relates to polyoxymethylene block copolymers obtainable by such a process and to the use thereof.

BACKGROUND

Block copolymers containing polyoxymethylene units alongside other polymer and polycondensate units are described, for example, in JP 2007 211082 A, WO 2004/096746 A1, GB 807589, EP 1 418 190 A1, U.S. Pat. Nos. 3,754,053, 3,575,930, US 2002/0016395, and JP 04-306215.

U.S. Pat. No. 3,575,930 describes the reaction of dihydroxy-terminated paraformaldehyde HO—$(CH_2O)_n$—H having n=2-64 with diisocyanates to give isocyanate-terminated polyoxymethylene polymers, which can be converted to polyurethane compounds in the reaction with diols.

JP 2007 211082 A describes the reaction of polyoxyalkylene polyols having an equivalent weight of ≥2500 with formaldehyde, formaldehyde oligomers or formaldehyde polymers to give polyoxymethylene-polyoxyalkylene block copolymers using anionic or cationic polymerization catalysts. The high molecular weight polyoxyalkylene polyol starters having low polydispersity used are prepared via double metal cyanide (DMC) catalysis. Because of the high molecular weight of the polyoxyalkylene polyols, the resultant polyoxymethylene-polyoxyalkylene block copolymers have a molecular weight of at least >5000 g/mol and are therefore less widely usable as a polyurethane unit. Furthermore, the direct reaction of the polyoxyalkylene polyols with the polyoxymethylene polymers via a melt-kneading method necessitates the use of high temperatures and corresponding specific high-viscosity apparatus (extruders, kneaders, etc.).

U.S. Pat. No. 3,754,053 describes polyoxymethylene-polyoxyalkylene block copolymers having a molecular weight of ≥10 000 g/mol. For preparation of copolymers having an inner polyoxymethylene block, in a first step, trioxane is converted to a polyoxymethylene prepolymer and the latter is then reacted with alkylene oxides in the presence of NaOH, for example, as polymerization catalyst. Here too, the polymers described are not very suitable for uses as a polyurethane unit because of their high molecular weight.

WO 2004/096746 A1 and US 2006/0205915 A1 disclose the reaction of formaldehyde oligomers with alkylene oxides and/or isocyanates. In this method, by means of the described use of formaldehyde oligomers HO—$(CH_2O)_n$—H, polyoxymethylene block copolymers having a relatively narrow molar mass distribution of n=2-19 are obtained, but the provision of the formaldehyde oligomers proceeding from aqueous formalin solution requires an additional process step for thermal removal. The formaldehyde oligomer solutions obtained in this context are not storage-stable, and so they then have to be processed further immediately. Moreover, these applications do not disclose differentiated activation conditions, for example the activation temperature, of the alkoxylation catalysts used, which are disadvantageous from safety and quality-relevant aspects among others for any possible industrial scale application because of undefined temperature peaks during the exothermic polymerization process (22.7 kcal/mol PO from M. Ionesco; Chemistry and Technology of Polyols for Polyurethanes, Rapra Techn. Ltd., 2005). Furthermore, only block copolymers having very short formaldehyde blocks are obtainable via this method.

EP 1 870 425 A1 discloses a process for preparing polyoxyalkylene-containing polyols by condensation of substituted or unsubstituted phenol structures with formaldehydes and/or other substituted alkanal structures. The resulting phenol-formaldehyde condensates are used here as polyol starters for the alkoxylation, although no repeat oxymethylene units are formed within these starter compounds.

In addition, resultant properties of the alkoxylated polyols containing aromatic systems differ fundamentally from aliphatic polyol structures because of the different chemical structures.

WO2012/091968 A1 claims a process for preparing polyetherols by polymerization of alkylene oxides onto starter compounds with the aid of DMC catalysts. In this case, the formaldehyde-associated structures disclosed are oligomeric phenol-formaldehyde condensates as corresponding starters, these differing fundamentally in structural terms from the polyoxymethylene starter structure.

SUMMARY

Proceeding from the prior art, the problem addressed was therefore that of providing a simple and economically advantageous process for preparing polyoxymethylene block copolymers based on oligomeric and polymeric forms of formaldehyde as starter substance, with which the problems that arise from the prior art can be overcome.

At the same time, the cleavage of the formaldehyde starter compounds used to smaller oligomers, oligomers and monomers and the formation of by-products and decomposition products was to be avoided as far as possible, and process safety was to be increased. In addition, stable low molecular weight polyoxymethylene block copolymers which have hydroxy-functionalized end groups and are suitable for the reaction with di- or polyisocyanates for preparation of polyurethanes were to be obtainable in this way. The process of the invention should preferably also be suitable for enabling access to polyoxymethylene-polyoxyalkylene carbonate block copolymers, achieving a high content of incorporated $CO_2$.

According to the invention, this problem is solved by a process for preparing polyoxymethylene block copolymers by catalytic addition of alkylene oxides and optionally further comonomers onto at least one polymeric formaldehyde starter compound having at least one terminal hydroxyl group, in the presence of a double metal cyanide (DMC) catalyst, wherein (i) in a first step the DMC catalyst is activated in the presence of the polymeric formaldehyde starter compound, activation of the DMC catalyst being accomplished by adding a portion (based on the totality of the amount of alkylene oxides used in the activation and polymerization) of one or more alkylene oxides ("activation"), (ii) in a second step one or more alkylene oxides and optionally further comonomers are added to the mixture resulting from step (i), where the alkylene oxides used in step (ii) may be the same as or different than the alkylene oxides used in step (i) ("polymerization"),
and wherein the activation of the DMC catalyst in the first step (i) is effected at an activation temperature ($T_{act}$) of 20 to 120° C.

The present invention further provides the polyoxymethylene block copolymers obtainable via the process of the invention, for the use thereof, and polyurethane polymers containing the polyoxymethylene block copolymers of the invention.

DETAILED DESCRIPTION

The use of the word "a" in connection with countable parameters should be understood here and hereinafter to mean the number one only when this is evident from the context (for example through the wording "exactly one"). Otherwise, expressions such as "an alkylene oxide", "a polymeric formaldehyde starter compound" etc. always refer to those embodiments in which two or more alkylene oxides, two or more polymeric formaldehyde starter compounds etc. are used.

The invention is illustrated in detail hereinafter. Various embodiments can be combined here with one another as desired, unless the opposite is apparent to the person skilled in the art from the context.

Polyoxymethylene block copolymers in the context of the invention refer to polymeric compounds which contain at least one polyoxymethylene block and at least one additional oligomeric block (for example polyoxyalkylene or polyoxyalkylene carbonate blocks) and preferably do not exceed a molecular weight in the four-digit range.

The resultant polyoxymethylene block copolymers offer a number of advantages over existing polymers. For instance, it is possible to control particular physical properties such as glass transition temperatures, melting ranges, viscosities and solubilities, etc. via the length of the polyoxymethylene blocks in relation to the other oligomeric blocks.

Compared to polyoxymethylene homopolymers of the same molecular weight, partial crystallinity in the polyoxymethylene block copolymers of the invention is typically lowered, which typically likewise leads to a lowering of glass transition temperatures, melting points and viscosities, etc. The presence of additional polyoxyalkylene blocks additionally leads typically to a distinct increase in the chemical and thermal stability. In addition, the polyoxymethylene block copolymers obtained generally have good solubilities in various solvents, are usually meltable readily and without loss of mass, or are already in the liquid state at low temperatures. Compared to polyoxymethylene homopolymers, the polyoxymethylene block copolymers thus exhibit much better processibility.

Compared to polyether polyols of the same molecular weight, the proportion of polyoxyalkylene units which are prepared from the corresponding alkylene oxides is reduced by the polyoxymethylene fraction, which contributes to an advantageous economic viability of the product. Various physical properties, such as glass transition temperatures, melting ranges, viscosities, solubility, etc., for a given molecular weight, can be controlled via the length of the polyoxymethylene blocks in relation to the polyoxyalkylene blocks, and via the molecular weight of the polymeric formaldehyde starter compound (polyoxymethylene block) used.

The synthetically variable molecular structure of the polyoxymethylene block copolymers obtained additionally enables the creation of tailored "hard-soft" segments at the molecular level. Compared to random polyoxymethylene-polyoxyalkylene copolymers, the polyoxymethylene block copolymers obtained have higher internal order because of their segment structure.

This may result in advantageous physical properties, particularly of conversion products of these polymers, and hence enable new applications.

Suitable polymeric formaldehyde starter compounds for the process of the invention are in principle those oligomeric and polymeric forms of formaldehyde having at least one terminal hydroxyl group for reaction with the alkylene oxides and any further comonomers. According to the invention, the term "terminal hydroxyl group" is understood to mean especially a terminal hemiacetal functionality which arises as a structural feature via the polymerization of formaldehyde. For example, the starter compounds may be oligomers and polymers of formaldehyde of the general formula HO—$(CH_2O)_n$—H where n is an integer$\geq 2$ and where polymeric formaldehyde typically has n>8 repeat units.

Polymeric formaldehyde starter compounds suitable for the process of the invention generally have molar masses of 62 to 30 000 g/mol, preferably of 62 to 12 000 g/mol, more preferably of 242 to 6000 g/mol and most preferably of 242 to 3000 g/mol, and comprise from 2 to 1000, preferably from 2 to 400, more preferably from 8 to 200 and most preferably from 8 to 100 repeat oxymethylene units. The starter compounds used in the process of the invention typically have a functionality (F) of 1 to 3, but in particular cases may also be of higher functionality, i.e. have a functionality of >3. Preference is given to using, in the process of the invention, open-chain polymeric formaldehyde starter compounds having terminal hydroxyl groups and having a functionality of 1 to 10, preferably of 1 to 5, more preferably of 2 to 3. Very particular preference is given to using, in the process of the invention, linear polymeric formaldehyde starter compounds having a functionality of 2. The functionality F corresponds to the number of OH end groups per molecule.

The preparation of the polymeric formaldehyde starter compounds which are used for the process of the invention can be effected by known processes (cf., for example, M. Haubs et al., 2012, Polyoxymethylenes, Ullmann's Encyclopedia of Industrial Chemistry; G. Reus et al., 2012, Formaldehyde, ibid.). The formaldehyde starter compounds can in principle also be used in the form of a copolymer in the process of the invention, in which case comonomers included in the polymer alongside formaldehyde are, for example, 1,4-dioxane or 1,3-dioxolane. Further suitable formaldehyde copolymers for the process of the invention are copolymers of formaldehyde and of trioxane with cyclic and/or linear formals, for example butanediol formal, or epoxides. It is likewise conceivable that comonomers incorporated into the formaldehyde polymer are higher homologous aldehydes, for example acetaldehyde, propionaldehyde, etc. It is likewise conceivable that formaldehyde starter compounds of the invention are again prepared proceeding from H-functional starter compounds; it is especially possible here, through the use of polyfunctional starter compounds, to obtain polymeric formaldehyde starter compounds having a hydroxy end group functionality F>2 (cf., for example, WO 1981001712 A1, Bull. Chem. Soc. J., 1994, 67, 2560-2566, U.S. Pat. No. 3,436,375, JP 03263454, JP 2928823).

For the process of the invention, it is also possible to use mixtures of different polymeric formaldehyde starter compounds or mixtures with other H-functional starter compounds. Suitable H-functional starter substances ("starters") used may be compounds having alkoxylation-active hydrogen atoms and having a molar mass of 18 to 4500 g/mol, preferably of 62 to 2500 g/mol and more preferably of 62 to 1000 g/mol. Groups active in respect of the alkoxylation and having active hydrogen atoms are, for example, —OH, —NH$_2$ (primary amines), —NH— (secondary amines), —SH, and —CO$_2$H, preferably —OH and —NH$_2$, more preferably —OH. H-Functional starter substances used are, for example, one or more compounds selected from the group consisting of mono- and polyhydric alcohols, polyfunctional amines, polyfunctional thiols, amino alcohols, thio alcohols, hydroxy esters, polyether polyols, polyester polyols, polyester ether polyols, polyethercarbonate polyols, polycarbonate polyols, polycarbonates, polyethyleneimines, polyetheramines, polytetrahydrofurans (e.g. PolyTHF® from BASF), polytetrahydrofuran amines, polyether thiols, polyacrylate polyols, castor oil, the mono- or diglyceride of ricinoleic acid, monoglycerides of fatty acids, chemically modified mono-, di- and/or triglycerides of fatty acids, and $C_1$-$C_{24}$ alkyl fatty acid esters containing an average of at least 2 OH groups per molecule.

As is well known, formaldehyde polymerizes merely as a result of the presence of small traces of water. In aqueous solution, therefore, depending on the concentration and temperature of the solution, a mixture of oligomers and polymers of different chain lengths forms, in equilibrium with molecular formaldehyde and formaldehyde hydrate. What is called paraformaldehyde precipitates out of the solution here as a white, sparingly soluble solid and is generally a mixture of linear formaldehyde polymers with n=8 to 100 repeat oxymethylene units.

One particular advantage of the process of the invention is that polymeric formaldehyde or what is called paraformaldehyde, which is available commercially and inexpensively, can be used directly as a starter compound without any need for additional preparatory steps here. In an advantageous embodiment of the invention, therefore, paraformaldehyde is used as starter compound. More particularly, it is possible via the molecular weight and end group functionality of the polymeric formaldehyde starter compound to introduce polyoxymethylene blocks of defined molar mass and functionality into the product.

Advantageously, it is possible here, in the process of the invention, to control the length of the polyoxymethylene block in a simple manner via the molecular weight of the formaldehyde starter compound used. Preference is given here to using linear formaldehyde starter compounds of the general formula HO—(CH$_2$O)$_n$—H where n is an integer≥2, preferably with n=2 to 1000, more preferably with n=2 to 400 and most preferably with n=8 to 100, having two terminal hydroxyl groups. More particularly, the starter compound used may also be mixtures of polymeric formaldehyde compounds of the formula HO—(CH$_2$O)$_n$—H each having different values of n. In an advantageous embodiment, the mixtures of polymeric formaldehyde starter compounds of the formula HO—(CH$_2$O)$_n$—H used contain at least 1% by weight, preferably at least 5% by weight and more preferably at least 10% by weight of polymeric formaldehyde compounds with n≥20.

By means of the process according to the invention, it is especially possible to obtain polyoxymethylene block copolymers having an A-B-A block structure comprising an inner polyoxymethylene block (B) and outer oligomeric blocks (A). It is likewise possible in accordance with the invention that formaldehyde starter compounds having a hydroxyl end group functionality F>2 are used, by means of which it is consequently possible to prepare homologous block structures B(—A)$_y$ having a number y>2 of outer oligomeric blocks (A) which results correspondingly from the functionality of the formaldehyde starter compound used. It is likewise possible in principle that formaldehyde starter compounds having a functionality F<2 are used; these may, for example, also be linear formaldehyde starter compounds with F=1 substituted at one end of the chain by a protecting group or by other chemical radicals.

A polyoxymethylene block in the context of the invention refers to a polymeric structural unit —(CH$_2$—O—)$_x$ where x is an integer≥2, containing at least one CH$_2$ group bonded to two oxygen atoms, which is bonded via at least one of the oxygen atoms to further methylene groups or other polymeric structures. Polyoxymethylene blocks —(CH$_2$—O—)$_x$ preferably contain an average of x≥2 to x≤1000, more preferably an average of x≥2 to x≤400 and especially preferably an average of x≥8 to x≤100 oxymethylene units. In the context of the invention, a polyoxymethylene block is also understood to mean those blocks containing small proportions of further monomeric and/or oligomeric units, generally less than 25 mol %, based on the totality of the monomer units present in the block.

Preferably, the outer oligomeric blocks (A) are polyoxyalkylene or polyoxyalkylene carbonate blocks, where polyoxyalkylene or polyoxyalkylene carbonate blocks in the context of the invention are also understood to mean those blocks including (small) proportions of further comonomers in the polymer, generally of less than 50 mol %, preferably less than 25 mol %, based on the total amount of all the repeat units present in the oligomeric block.

A polyoxyalkylene carbonate block in the context of the invention refers to a polymeric structural unit —O[(C$_2$R$^1$R$^2$R$^3$R$^4$O)$_x$(CO$_2$(C$_2$)(C$_2$R$^1$R$^2$R$^3$R$^4$O)]$_z$— with x≥1, y≥0 and z≥1, where R$^1$, R$^2$, R$^3$ and R$^4$ are each independently hydrogen, an alkyl or aryl radical optionally containing additional heteroatoms such as nitrogen, oxygen, silicon, sulfur or phosphorus and may differ in different repeat units. The term "alkyl" in the context of the overall invention generally includes substituents from the group of n-alkyl such as methyl, ethyl or propyl, branched alkyl and/or cycloalkyl. The term "aryl" in the context of the overall invention generally includes substituents from the group of monocyclic carbo- or heteroaryl substituents such as phenyl and/or polycyclic carbo- or heteroaryl substituents, which may optionally be substituted by further alkyl groups and/or heteroatoms such as nitrogen, oxygen, silicon, sulfur or phosphorus. The R$^1$, R$^2$, R$^3$ and/or R$^4$ radicals may be joined to one another within a repeat unit such that they form cyclic structures, for example a cycloalkyl radical incorporated into the polymer chain via two adjacent carbon atoms.

It is possible by the process of the invention, proceeding from formaldehyde starter compounds present as a mixture of different polymer chain lengths, for example paraformaldehyde, to obtain polyoxymethylene copolymers having a low content of by-products and decomposition products and a narrow molecular weight distribution. Without wishing to be bound to a particular theory, it can be assumed that, during the step of activating the DMC catalyst, there is likewise conditioning of the formaldehyde starter compound, preventing the formation of by-products and decomposition products (for example formates, methoxy derivatives, monomeric formaldehyde) and defragmentation of the polymeric formaldehyde to give shorter chain lengths and simultaneously achieving sufficient activity and selectivity of the catalyst. This involves conversion of the formaldehyde starter compound present in thermally and chemically labile and usually insoluble hemiacetal form by the reaction with the alkylene oxide to a thermally and chemically stable form. Surprisingly, the step of activation of the DMC catalyst can be combined with the conditioning of the polymeric formaldehyde starter and can be performed in a particularly advantageous manner at unexpectedly mild temperatures. Nothing of this kind was to be expected, since DMC catalysts typically require much higher temperatures, for example of 130° C., for activation. The conditioning of the formaldehyde starter compound in the presence of the DMC catalyst enables reaction of the starter with alkylene oxides and any further comonomers in the subsequent polymerization step at higher reaction temperatures as well, without any further defragmentation and/or the formation of by-products and decomposition products. A further advantage is that the conditioned formaldehyde starter compound usually has much higher solubility after the conditioning, such that only small amounts of or no further solvents and/or suspension media are required.

Moreover, it can be ensured by the process of the invention that an active DMC catalyst system for the polymerization is present, and a constantly progressing polymerization with continuous addition of the comonomers ensures a safe process and high product quality.

According to the invention, the DMC catalyst is therefore activated in the presence of the polymeric formaldehyde starter compound. The starter compound and the DMC catalyst may optionally be suspended here in a suspension medium. It is likewise also possible to use a further liquid starter compound ("co-starter") in the mixture, in which case the DMC catalyst and the polymeric formaldehyde starter compound are suspended therein.

According to the invention, the DMC catalyst is activated at an activation temperature $T_{act}$ in the range from 20 to 120° C., preferably at 30 to 120° C., more preferably at 40 to 100° C. and most preferably at 60 to 100° C.

"Activation" of the DMC catalyst is understood to mean a step in which a portion of alkylene oxide is added to the DMC catalyst suspension at the specific activation temperature and then the addition of the alkylene oxide is stopped, with observation of evolution of heat because of an exothermic chemical reaction which follows, which can lead to a temperature spike ("hotspot"), and of a pressure drop in the reactor because of the conversion of alkylene oxide.

DMC catalysts suitable for the process of the invention for use in the homopolymerization of alkylene oxides are known in principle from the prior art (see, for example, U.S. Pat. Nos. 3,404,109, 3,829,505, 3,941,849 and 5,158,922). DMC catalysts, which are described, for example, in U.S. Pat. No. 5,470,813, EP-A 700 949, EP-A 743 093, EP-A 761 708, WO 97/40086, WO 98/16310 and WO 00/47649, have very high activity in the polymerization of alkylene oxides and, if appropriate, the copolymerization of alkylene oxides with suitable comonomers and enable the preparation of polyoxymethylene copolymers at very low catalyst concentrations, such that removal of the catalyst from the finished product is generally not required. A typical example is that of the highly active DMC catalysts which are described in EP-A 700 949 and contain not only a double metal cyanide compound (e.g. zinc hexacyanocobaltate(III)) and an organic complex ligand (e.g. tert-butanol) but also a polyether having a number-average molecular weight greater than 500 g/mol.

The concentration of DMC catalyst used is 10 to 10 000 ppm, more preferably 20 to 5000 ppm and most preferably 50 to 2000 ppm, based on the mass of the polyoxymethylene block copolymer to be prepared. According to the profile of requirements for the downstream use, the DMC catalyst can be left in the product or (partly) removed. The (partial) removal of the DMC catalyst can be effected, for example, by treatment with adsorbents and/or filtration. Methods of removing DMC catalysts are described, for example, in U.S. Pat. No. 4,987,271, DE-A-3132258, EP-A-0 406 440, U.S. Pat. Nos. 5,391,722, 5,099,075, 4,721,818, 4,877,906 and EP-A-0 385 619.

Epoxides (alkylene oxides) used for the preparation of the polyoxymethylene block copolymers are compounds of the general formula (I):

where $R^1$, $R^2$, $R^3$ and $R^4$ are each independently hydrogen or an alkyl or aryl radical optionally containing additional heteroatoms such as nitrogen, oxygen, silicon, sulfur or phosphorus and may optionally be joined to one another such that they form cyclic structures such as a cycloalkylene oxide for example.

In the context of the process of the invention, it is possible in principle to use those alkylene oxides which are suitable for the polymerization in the presence of a DMC catalyst. If various alkylene oxides are used, they can be metered in either as a mixture or successively. In the case of the latter metering method, the polyether chains of the polyoxymethylene-polyoxyalkylene block copolymer obtained in this way may themselves likewise have a block structure.

In general, it is possible to use alkylene oxides (epoxides) having 2-24 carbon atoms for the process of the invention. The alkylene oxides having 2-24 carbon atoms are, for example, one or more compounds selected from the group consisting of ethylene oxide, propylene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, mono- or polyepoxidized fats as mono-, di- and triglycerides, epoxidized fatty acids, $C_1$-$C_{24}$ esters of epoxidized fatty acids, epichlorohydrin, glycidol, and derivatives of glycidol, for example methyl glycidyl ether, ethyl glycidyl ether, 2-ethylhexyl glycidyl ether, allyl glycidyl ether, glycidyl methacrylate and epoxy-functional alkoxysilanes, for example 3-glycidyloxypropyltrimethoxysilane, 3-glycidyloxypropyltriethoxysilane, 3-glycidyloxypropyltripropoxysilane, 3-glycidyloxypropylmethyldimethoxysilane, 3-glycidyloxypropylethyldiethoxysilane, 3-glycidyloxypropyltriisopropoxysilane. The epoxide of the general formula (I) is preferably a terminal epoxide where $R^1$, $R^2$ and $R^3$ are hydrogen, and $R^4$ may be hydrogen, an alkyl or aryl radical optionally containing additional heteroatoms such as nitrogen, oxygen, silicon, sulfur or phosphorus and may differ in different repeat units. Preferably, the alkylene oxides used are ethylene oxide and/or propylene oxide, especially propylene oxide.

Preferably, the process of the invention is conducted in such a way that the activation of the catalyst and the conditioning of the polymeric formaldehyde starter compound in step ((3) are followed by a polymerization step (γ) with metered addition of one or more alkylene oxides. In principle, the process can also be ended after step ((3), such that the conditioned polymeric formaldehyde starter compound then constitutes the end product of the process. The latter generally has a high stability by virtue of the conditioning of the invention and can be used analogously to the polyoxymethylene block copolymer obtained from step (γ), if desired, as an OH-functional unit for various further reactions.

In a further embodiment of the process of the invention, the polymerization of the alkylene oxides is effected in the presence of a further comonomer. Further comonomers used may, for example, be any oxygen-containing cyclic compounds, especially cyclic ethers, for example oxetane, THF, dioxane or cyclic acetals, for example 1,3-dioxolane or 1,3-dioxepane, cyclic esters, for example γ-butyrolactone, γ-valerolactone, ε-caprolactone, or cyclic acid anhydrides, for example maleic anhydride, glutaric anhydride or phthalic anhydride, and carbon dioxide. Preference is given to using carbon dioxide as comonomer.

The metered addition of further comonomers can be effected in neat form, in solution or as a mixture with one or more alkylene oxides. The metered addition of further comonomers can likewise be effected in parallel with the metered addition or after the metered addition of the alkylene oxides.

In a preferred embodiment of the process of the invention, as well as the addition of the alkylene oxide(s) onto the polymeric formaldehyde starter compound, carbon dioxide ($CO_2$) is added on as a further comonomer. In this way, it is possible to prepare polyoxymethylene-polyoxyalkylene carbonate copolymers.

Compared to existing products (for example polyether polyols in the polyurethane sector or polyoxymethylene (co-)polymers in the POM sector), these additionally include $CO_2$ as an inexpensive and environmentally friendly comonomer. Since $CO_2$ is, inter alia, a waste product from energy generation from fossil raw materials and is being sent here to a new chemical utilization, the incorporation of $CO_2$ into the polymer structures results in not only economic but also environmental benefits (favorable $CO_2$ balance of the product polymers, etc.).

Polyoxymethylene-polyoxyalkylene carbonate block copolymers in the context of the invention refer to polymeric compounds containing at least one polyoxymethylene block and at least one polyoxyalkylene carbonate block. Polyoxymethylene-polyoxyalkylene carbonate block copolymers are of particular interest as feedstocks in the polyurethane sector, and for applications in the polyoxymethylene (POM) sector. By altering the $CO_2$ content, the physical properties can be matched to the particular use, as a result of which it is possible to develop new fields of use for these block copolymers. More particularly, it is possible via the process of the invention to provide polyoxymethylene-polyoxyalkylene carbonate copolymers wherein a high content of incorporated $CO_2$ is achieved, and the products have comparatively low polydispersity and contain a very low level of by-products and decomposition products of the polymeric formaldehyde.

European patent application EP13171772.0 discloses a process for preparing polyoxyalkylene carbonate-polyoxymethylene block copolymers, wherein polyoxyalkylene carbonates having Zerewitinoff-active hydrogen atoms as starter compounds are converted with addition polymerization of gaseous monomeric formaldehyde. By means of this process, however, it is not possible to form polyoxymethylene-polyoxyalkylene carbonate block copolymers having inner polyoxymethylene blocks, and the products obtained from the polymerization with monomeric formaldehyde have to be reacted in an additional step with epoxides or cyclic carboxylic or carbonic esters in order to obtain stable products having terminal functionalities.

There follows a detailed description of several variants for performance of the process of the invention for preparing polyoxymethylene block copolymers by addition of alkylene oxides and optionally further comonomers onto polymeric formaldehyde starter compounds. The illustration is merely illustrative and should not be understood such that it restricts the present invention.

For example, the process of the invention is characterized in that in the first step (i)
(α) a suspension medium or a polymeric formaldehyde starter compound is initially charged and, optionally, water and/or other volatile compounds are removed by means of elevated temperature and/or reduced pressure ("drying"), the DMC catalyst being added to the polymeric formaldehyde starter compound or to the suspension medium before or after the drying,
(β) activation of the DMC catalyst in the presence of the polymeric formaldehyde starter compound is accomplished by adding a portion (based on the entirety of the amount of alkylene oxides used in the activation and polymerization) of one or more alkylene oxides to the mixture resulting from step (α), where this portion of alkylene oxide may optionally be added in the presence of further comonomers such as $CO_2$ in particular and where the temperature spike ("hotspot") which occurs due to the exothermic chemical reaction that follows and/or a pressure drop in the reactor is then awaited in each case, and where step (β) for activation may also be repeated,
and in the second step (ii)
(γ) one or more alkylene oxides and optionally further comonomers, especially carbon dioxide, are added to the mixture resulting from step (β), where the alkylene oxides used in step (γ) may be the same as or different than the alkylene oxides used in step (β) ("polymerization"),
wherein at least one polymeric formaldehyde starter compound is added at least in one of steps (α) and (β).

The polymeric formaldehyde starter compound can be initially charged here together with the DMC catalyst and the suspension medium in step (α), or preferably after the drying, no later than in step (β).

Any suspension media used generally do not contain any H-functional groups. Suitable suspension media are any polar aprotic, weakly polar aprotic and nonpolar aprotic solvents, none of which contain any H-functional groups. The suspension medium used may also be a mixture of two or more of these suspension media. The following polar aprotic suspension media are mentioned here by way of example: 4-methyl-2-oxo-1,3-dioxolane (also referred to hereinafter as cyclic propylene carbonate or cPC), 1,3-dioxolan-2-one (also referred to hereinafter as cyclic ethylene carbonate or cEC), acetone, methyl ethyl ketone, acetonitrile, nitromethane, dimethyl sulfoxide, sulfolane, dimethylformamide, dimethylacetamide and N-methylpyrrolidone. The group of the nonpolar and weakly polar aprotic suspension media includes, for example, ethers, for example dioxane, diethyl ether, methyl tert-butyl ether and tetrahydrofuran, esters, for example ethyl acetate and butyl acetate, hydrocarbons, for example pentane, n-hexane, benzene and alkylated benzene derivatives (e.g. toluene, xylene, ethylbenzene) and chlorinated hydrocarbons, for example chloroform, chlorobenzene, dichlorobenzene and carbon tetrachloride. Preferred suspension media are 4-methyl-2-oxo-1,3-dioxolane, 1,3-dioxolan-2-one, toluene, xylene, ethylbenzene, chlorobenzene and dichlorobenzene, and mixtures of two or more of these suspension media; particular preference is given to 4-methyl-2-oxo-1,3-dioxolane and 1,3-dioxolan-2-one and toluene or a mixture of 4-methyl-2-oxo-1,3-dioxolane and 1,3-dioxolan-2-one and/or toluene. It is likewise also possible to use, as suspension medium, a further starter compound which is in liquid form under the reaction conditions, in a mixture with the polymeric formaldehyde starter compound.

Step ($\alpha$): (Drying)

The addition of the individual components in step ($\alpha$) can be effected simultaneously or successively in any sequence.

Preferably, in step ($\alpha$), a suspension medium containing no H-functional groups is initially charged in the reactor. Subsequently, the amount of DMC catalyst required for the polymerization, which is preferably unactivated, is introduced into the reactor. The sequence of addition is not crucial. It is also possible first to introduce the DMC catalyst and then the suspension medium into the reactor. Alternatively, it is also possible first to suspend the DMC catalyst in the suspension medium and then to introduce the suspension into the reactor. The suspension medium provides a sufficient heat transfer area with the reactor wall or cooling elements installed in the reactor, such that the heat of reaction released can be removed very efficiently. Moreover, the suspension medium, in the event of a cooling failure, provides heat capacity, such that the temperature in this case can be kept below the breakdown temperature of the reaction mixture. Alternatively, it is also possible in step ($\alpha$) to initially charge a suspension medium containing no H-functional groups and additionally a portion of the polymeric formaldehyde starter compound and optionally DMC catalyst in the reactor, or it is also possible in step ($\alpha$) to initially charge a portion of the polymeric formaldehyde starter compound and optionally DMC catalyst in the reactor. In addition, it is also possible in step ($\alpha$) to initially charge the total amount of the polymeric formaldehyde starter compound and optionally DMC catalyst in the reactor.

The polymeric formaldehyde starter compound may be initially charged here, in principle, as a mixture with further polymeric formaldehyde starter compounds or other H-functional starter compounds.

The process can be conducted in such a way that, in step ($\alpha$), a suspension medium, the polymeric formaldehyde starter compound and the DMC catalyst are initially charged and, optionally, water and/or other volatile compounds are removed by means of elevated temperature and/or reduced pressure ("drying") or, in an alternative embodiment, step ($\alpha$) is conducted in such a way that, in a step ($\alpha$1), a suspension medium and the DMC catalyst are initially charged and, optionally, water and/or other volatile compounds are removed by means of elevated temperature and/or reduced pressure ("drying") and, in a subsequent step ($\alpha$2), the formaldehyde starter compound is added to the mixture from step ($\alpha$1). The addition of the polymeric formaldehyde starter compound may follow cooling of the reaction mixture from step ($\alpha$1), especially at room temperature, or the reaction mixture may already be brought to the temperature that prevails in the subsequent step ($\beta$) and the addition may be effected at this temperature. The formaldehyde starter compound is generally added under inert conditions.

The DMC catalyst is preferably used in an amount such that the content of DMC catalyst in the resulting reaction product is 10 to 10 000 ppm, more preferably 20 to 5000 ppm, and most preferably 50 to 2000 ppm.

In a preferred embodiment, inert gas (for example argon or nitrogen), an inert gas/carbon dioxide mixture or carbon dioxide is introduced into the resulting mixture of suspension medium and DMC catalyst and/or the polymeric formaldehyde starter compound at a temperature of 90° C. to 150° C., more preferably of 100° C. to 140° C., and at the same time a reduced pressure (absolute) of 10 mbar to 800 mbar, more preferably of 50 mbar to 200 mbar, is applied.

In an alternative preferred embodiment, the resulting mixture of DMC catalyst with suspension medium and/or the polymeric formaldehyde starter compound, at a temperature of 90° C. to 150° C., more preferably of 100° C. to 140° C., is contacted at least once, preferably three times, with 1 bar to 100 bar (absolute), more preferably 3 bar to 50 bar (absolute), of an inert gas (for example argon or nitrogen), an inert gas/carbon dioxide mixture or carbon dioxide and then the gauge pressure is reduced in each case to about 1 bar to 20 bar (absolute).

The DMC catalyst may be added, for example, in solid form or in the form of a suspension in a suspension medium or two or more suspension media or—if the polymeric formaldehyde starter compound is in a liquid state of matter—as a suspension in a polymeric formaldehyde starter compound.

Step ($\beta$): (Activation)

Step ($\beta$) serves to activate the DMC catalyst. This step may optionally be conducted under an inert gas atmosphere, under an atmosphere of inert gas/carbon dioxide mixture or under a carbon dioxide atmosphere. Activation in the context of this invention refers to a step in which a portion of alkylene oxide is added to the DMC catalyst suspension at temperatures of 20 to 120° C. ("activation temperature") and then the addition of the alkylene oxide is stopped, with observation of evolution of heat because of an exothermic chemical reaction which follows, which can lead to a temperature spike ("hotspot"), and of a pressure drop in the reactor because of the conversion of alkylene oxide and optionally $CO_2$.

In a preferred embodiment, the amount of one or more alkylene oxides used in the activation in step ($\beta$) is 2 to 100 molar equivalents, preferably 4 to 50 molar equivalents, more preferably 4.5 to 25 molar equivalents, based on the molar amount of polymeric formaldehyde starter compound used, using the number-average molecular weight ($M_n$) of the formaldehyde starter compound or of the mixtures used as the basis. The alkylene oxide can be added in one step or stepwise in two or more portions. Preferably, after addition of a portion of alkylene oxide, the addition of the alkylene oxide is stopped until the occurrence of evolution of heat and only then is the next portion of alkylene oxide added.

For the process of the invention, it has additionally been found that the activation (step ($\beta$)) in the presence of the polymeric formaldehyde starter compound for preparation of the polyoxymethylene block copolymers is conducted advantageously at an activation temperature $T_{act}$ of 20 to 120° C., preferably at 30 to 120° C., more preferably at 40 to 100° C. and most preferably at 60 to 100° C. According to the invention, the evolution of heat resulting from the chemical reaction in the activation of the DMC catalyst preferably does not lead to exceedance of a temperature of 120° C. in the reaction vessel. Below 20° C., the reaction proceeds only very slowly, and activation of the DMC catalyst takes a disproportionately long time or may not take place to the desired degree. At temperatures of 130° C. or higher, there is a significant rise in the amount of unwanted by-products/decomposition products of polymeric formaldehyde starter compounds. For example, the formation of formate and methoxy traces is observed. It has additionally been found to be an advantage of this embodiment that it is likewise possible via exact adjustment of the parameters within this range to influence the properties of the polyoxymethylene block copolymer obtained, especially the length of the polyoxymethylene block.

The process step of activation is the period of time from the addition of the portion of alkylene oxide, optionally in the presence of $CO_2$, to the reaction mixture comprising a suspension medium, DMC catalyst and the formaldehyde starter compound until the occurrence of the evolution of heat (exothermicity). Optionally, the portion of the alkylene oxide can be added to the reaction mixture in a plurality of individual steps, optionally in the presence of $CO_2$, and then the addition of the alkylene oxide can be stopped in each case. In this case, the process step of activation comprises the period from the addition of the first portion of alkylene oxide, optionally in the presence of $CO_2$, to the reaction mixture until the occurrence of the evolution of heat after addition of the last portion of alkylene oxide. In general, the activation step may be preceded by a step for drying the DMC catalyst and optionally the polymeric formaldehyde starter compound at elevated temperature and/or reduced pressure, optionally with passage of an inert gas through the reaction mixture, in which case this step of drying is not part of the activation step in the context of the present invention.

The metered addition of one or more alkylene oxides (and optionally the further comonomers, especially carbon dioxide) can in principle be effected in different ways. The commencement of the metered addition can be effected from the reduced pressure or at a previously chosen supply pressure. The supply pressure is preferably established by introduction of an inert gas (for example nitrogen or argon) or of carbon dioxide, where the pressure (in absolute terms) is 5 mbar to 100 bar, preferably 10 mbar to 50 bar and by preference 20 mbar to 50 bar. Another alternative embodiment is a two-stage activation (step β), wherein (β-I) in a first activation stage a first portion of alkylene oxide is added under inert gas atmosphere and (β-II) in a second activation stage a second portion of alkylene oxide is added under carbon dioxide atmosphere, wherein the polymeric formaldehyde starter compound may be added before and after component step (β-I).

Step (γ): (Polymerization)

The metered addition of one or more alkylene oxides can be effected simultaneously or sequentially, each via separate metering sites (addition sites) or via one or more metering sites. If two or more alkylene oxides are used for synthesis of the polyoxymethylene block copolymers, the alkylene oxides can be metered in individually or as a mixture.

For the process of the invention, it has been found that the polymerization for preparation of the polyether block in the polyoxymethylene-polyoxyalkylene block copolymers (step (γ)) is advantageously conducted at 50 to 150° C., preferably at 60 to 145° C., more preferably at 70 to 140° C. and most preferably at 90 to 130° C. If temperatures below 50° C. are set, the reaction proceeds disproportionately slowly. At temperatures above 150° C., the amount of unwanted by-products rises significantly.

In a further embodiment of the process of the invention, the polymerization is effected in the presence of at least one comonomer. The metered addition of the further comonomers can be effected in neat form, in solution or otherwise in any industry realizable forms. The metered addition of one or more alkylene oxides and the comonomers can be effected simultaneously or sequentially, it being possible to add the total amount of comonomer all at once or by metered addition over the reaction time. In a preferred embodiment of the invention, carbon dioxide is metered in as a comonomer. The metered addition of one or more alkylene oxides is effected simultaneously or sequentially with the metered addition of carbon dioxide. Via the manner of metered addition of the alkylene oxides and the comonomers, preferably carbon dioxide, it is possible to synthesize polyoxymethylene block copolymers having random, alternating, block-type or gradient-type polyether and/or polyoxyalkylene carbonate blocks.

In the preparation of the polyoxymethylene-polyoxyalkylene carbonate block copolymers with copolymerization of $CO_2$ as a comonomer, preference is given to using an excess of carbon dioxide based on the expected or estimated amount of carbon dioxide incorporated into the polyoxyalkylene carbonate block, since an excess of carbon dioxide is advantageous as a result of the inertness of carbon dioxide. The amount of carbon dioxide can be fixed via the total pressure under the respective reaction conditions. An advantageous total pressure (in absolute terms) for the copolymerization for preparation of the polyoxyalkylene carbonate block has been found to be in the range from 0.01 to 120 bar, preferably 0.1 to 110 bar, particularly preferably from 1 to 100 bar. For the process of the invention, it has additionally been found that the copolymerization for preparation of the polyoxyalkylene carbonate block is conducted advantageously at 50 to 150° C., preferably at 60 to 145° C., more preferably at 70 to 140° C. and most preferably at 90 to 130° C. If temperatures below 50° C. are set, the reaction proceeds disproportionately slowly. At temperatures above 150° C., the amount of unwanted by-products rises significantly. It should also be noted that the $CO_2$, given the choice of pressure and temperature, is converted from the gaseous state as far as possible to the liquid and/or supercritical fluid state. However, $CO_2$ can also be added to the reactor in solid form and then be converted under the selected reaction conditions to the liquid and/or supercritical fluid state.

Carbon dioxide can be used in the gaseous, solid, liquid or supercritical state, preferably in the gaseous or solid state, more preferably in the gaseous state. In the case of use of carbon dioxide in the gaseous state, a partial carbon dioxide pressure of 1 to 73.8 bar, preferably of 1 to 60 bar, more preferably of 5 to 50 bar, is chosen. The combination of pressure and temperature in the case of use of gaseous carbon dioxide is chosen such that carbon dioxide as a pure substance is in the gaseous state under the chosen reaction conditions. The corresponding conditions can be inferred from the phase diagram. After introduction of gaseous carbon dioxide into the reactor, it dissolves partly or fully in the reaction mixture.

The three steps (α), (β) and (γ) can be performed in the same reactor, or each can be performed separately in different reactors. Particularly preferred reactor types for the process of the invention are stirred tanks, tubular reactors, and loop reactors. In addition, it is also possible to use extruders, kneaders, etc. as preferred reactors for the process of the invention. If the reaction steps α, β and γ are performed in different reactors, a different reactor type can be used for each step. In the case of a completely continuous reaction regime, the individual steps should preferably be spatially separated from one another, or steps (α) and (β) from (γ), such that a separate temperature regime and a suitable gas supply and application of reduced pressure, addition of polymeric formaldehyde and metered addition of monomers in the individual steps is possible in accordance with the invention.

Because of their thermal and chemical stability, the polyoxymethylene block copolymers of the invention, or the product mixtures obtained from the process, can be worked up especially by distillation. It is preferable here to use thin-film evaporators, strand evaporators and stripping columns and combinations thereof to remove solvents or suspension media, volatile constituents and unreacted monomers and/or oligomers. However, all other apparatuses are also suitable in principle for thermal distillative workup. This mode of workup can be effected continuously or batchwise, and in parallel to or after the reaction.

The present invention further provides polyoxymethylene block copolymers obtainable by the process of the invention.

The molecular weight of the polyoxymethylene block copolymers of the invention is especially the product of addition of the molecular weight of the polymeric formaldehyde starter compound and the addition-polymerized blocks. In one embodiment, the polyoxymethylene block copolymers have a number-average molecular weight of ≤15 000 g/mol, preferably ≤9500 g/mol, more preferably ≤6000 g/mol, even more preferably ≤5000 g/mol, especially of 200 g/mol to 9500 g/mol, preferably of 500 g/mol to 5000 g/mol. The number-average molecular weight can be determined, for example, by gel permeation chromatography (GPC) against, for example, polystyrene standards and/or via experimentally determined hydroxyl numbers (OH #).

The polyoxymethylene block copolymers obtainable via the process of the invention have a block structure comprising an inner polyoxymethylene block (B) comprising at least two and at most 1000 oxymethylene units, preferably at least 2 and at most 400 oxymethylene units, more preferably from 8 to 200 and most preferably at least 8 and at most 100 oxymethylene units, and at least one outer oligomeric block (A) preferably comprising a proportion of at least 25 mol %, more preferably at least 50 mol %, of polyoxyalkylene units, based on the total amount of all oligomer units in this block. The number of outer oligomeric blocks (A) results correspondingly from the functionality of the formaldehyde starter compound used. Preferably, the polyoxymethylene-polyoxyalkylene block copolymer consists exclusively of the blocks A and B. In an advantageous embodiment, the outer oligomeric block is a polyoxyalkylene block, more preferably a polyoxyalkylene carbonate block.

The polyoxymethylene block copolymers of the invention preferably have terminal hydroxyl groups and preferably have a functionality F≥2 (number of hydroxyl groups per molecule).

In a further embodiment of the polyoxymethylene block copolymers, these have a monomodal molecular weight distribution and a polydispersity index (PDI) of ≤2.5, preferably ≤2.2.

The polyoxymethylene block copolymers obtainable by the process of the invention preferably contain less than 2% by weight, especially less than 1% by weight, based on the total mass of the polyoxymethylene block copolymer obtained, of formate and/or methoxy impurities.

The invention likewise provides a polyoxymethylene-polyoxyalkylene carbonate block copolymer comprising an inner polyoxymethylene block ("starter") and at least one outer polyoxyalkylene carbonate block of formula (II)

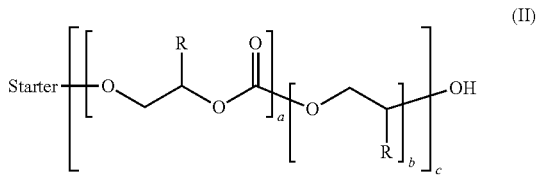

where R is an organic radical such as alkyl, alkylaryl, arylalkyl or aryl, each of which may also contain heteroatoms, for example O, S, Si, etc.,
and where a, b and c are each an integer and R may differ in different repeat units,
and where the structural unit "starter" represents a polyoxymethylene block deriving from the polymeric formaldehyde starter compound,
and where the product shown here in scheme (II) for the polyoxymethylene-polyoxyalkylene carbonate block copolymer should be understood merely such that blocks having the structure shown may in principle be found in the polyoxymethylene-polyoxyalkylene carbonate block copolymer obtained, but the sequence, number and length of the blocks and the OH functionality of the "starter" may vary and is not restricted to the polyoxymethylene-polyoxyalkylene block copolymer shown in scheme (II).

The polyoxymethylene block copolymers obtainable by the process of the invention generally have a low content of by-products and decomposition products, such as formate, methoxy traces, monomeric and oligomeric formaldehyde and residual monomers, and can be processed without any problem, especially by reaction with di-, tri- and/or polyisocyanates to give polyurethanes, isocyanate-functionalized polyurethane prepolymers or polyisocyanurates, especially polyurethane thermoplastics, polyurethane coatings, fibers, elastomers or adhesives, and especially also polyurethane foams including flexible foams (for example flexible slabstock polyurethane foams and flexible molded polyurethane foams) and rigid foams. For polyurethane applications, preference is given to using polyoxymethylene block copolymers having a functionality of at least 2. In addition, the polyoxymethylene block copolymers obtainable by the process of the invention can be used in applications such as washing and cleaning composition formulations, adhesives, paints, varnishes, functional fluids, drilling fluids, fuel additives, ionic and nonionic surfactants, lubricants, process chemicals for papermaking or textile manufacture, or cosmetic/medical formulations. The person skilled in the art is aware that, depending on the respective field of use, the polymers to be used have to fulfill certain material properties, for example molecular weight, viscosity, polydispersity, functionality and/or hydroxyl number (number of terminal hydroxyl groups per molecule).

The invention therefore likewise relates to the use of polyoxymethylene block copolymers of the invention for preparation of polyurethane polymers. In one embodiment of said use, the polyurethane polymers are flexible polyurethane foams or rigid polyurethane foams. In a further embodiment of said use, the polyurethane polymers are thermoplastic polyurethane polymers.

The invention therefore likewise provides a polyurethane polymer obtainable by reaction of a di-, tri- and/or polyisocyanate with at least one polyoxymethylene block copolymer of the invention.

The invention likewise provides a flexible polyurethane foam or a rigid polyurethane foam obtainable by reaction of a di-, tri- and/or polyisocyanate with at least one polyoxymethylene block copolymer of the invention.

The invention also includes the use of polyoxymethylene block copolymers according to the present invention for production of polyurethanes, washing and cleaning composition formulations, drilling fluids, fuel additives, ionic and nonionic surfactants, lubricants, process chemicals for papermaking or textile production, or cosmetic formulations.

EXAMPLES

Compounds Used:

Paraformaldehyde from Ineos was used. Propylene oxide was sourced from Sigma-Aldrich and used without purification. The DMC catalyst used in all examples was DMC catalyst prepared according to example 6 in WO 01/80994 A1, containing zinc hexacyanocobaltate, tert-butanol and polypropylene glycol having a number-average molecular weight of 1000 g/mol.

Example 1: Preparation of a Polyoxymethylene-Polyoxyalkylene Carbonate Block Copolymer ($T_{act}$=40° C.)

In a 300 mL pressure reactor with a gas and liquid metering unit, 65 mg of nonactivated DMC catalyst were suspended in 30 g of toluene. The suspension was heated to 130° C. while stirring, $N_2$ was injected to 40 bar and then the $N_2$ pressure was lowered to 15 bar. The injection and release of $N_2$ was conducted twice more in the same way. The suspension thus obtained was cooled down to room temperature and the $N_2$ pressure was released. The pressure reactor was then opened and 15 g of paraformaldehyde (pFA) were added to the suspension present. Once the reactor had been closed and heated to 40° C. ($T_{act}$) while stirring (1200 rpm), 15 g of propylene oxide (PO) were added at a metering rate of 10 g/min. The commencement of the reaction was manifested by a pressure drop to the starting pressure and a slight increase in temperature. On completion of activation, at a temperature of 100° C. and 50 bar of carbon dioxide ($CO_2$), 75 g of PO were added continuously at a metering rate of 1 g/min and while stirring (1200 rpm). The progress of the reaction was observed by means of $CO_2$ consumption while keeping the pressure in the reactor constant at 50 bar by continuous further metered addition. After the addition of PO had ended, stirring was continued at 100° C. and reaction pressure for 2 h (1200 rpm). This was followed by cooling down to room temperature. The reaction mixture was analyzed by means of NMR and GPC analysis and the results are shown in table 1.

The composition of the polymer was determined by means of $^1$H NMR (Bruker DPX 400, 400 MHz; pulse program zg30, relaxation time D1: 10 s, 64 scans). Each sample was dissolved in deuterated chloroform. The relevant resonances in the $^1$H-NMR (based on TMS=0 ppm) and the assignment of the area integrals (A) are as follows:

cyclic propylene carbonate (cPC), by-product, with resonance at 4.5 ppm, area integral corresponds to one hydrogen atom;

linear propylene carbonate in the polymer (lPC) with resonances at 1.2 to 1.4 ppm, area integral minus 3 hydrogen atoms of monomeric propylene oxide (PO) thus corresponds to 3 hydrogen atoms;

monomeric propylene oxide (PO) which has not been fully depleted, with resonance at 2.4 or 2.75 ppm, area integral corresponds to one hydrogen atom in each case;

polypropylene oxide (PPO), PO homopolymer, with resonances at 1.0 to 1.2 ppm, area integral corresponds to 3 hydrogen atoms;

poly- or paraformaldehyde (pFA) with resonances at 4.6 to 5.2 ppm, area integral minus one hydrogen atom each of cyclic propylene carbonate (cPC) and of linear propylene carbonate (lPC) thus corresponds to 2 hydrogen atoms;

formate (HCOO), by-product, with resonance at 8.1 ppm, area integral corresponds to one hydrogen atom;

methoxy (MeO), by-product in traces, with resonance at 3.4 ppm.

The mole fractions (x) of the reaction mixture are determined as follows:

x(cPC)=A(4.5 ppm)
x(lPC)=A(1.2-1.4 ppm)−(3·x(PO))
x(PO)=A(2.75 ppm) or A(2.4 ppm)
x(PPO)=A(1.0-1.2 ppm)/3
x(pFA)=(A(4.6-5.2 ppm)−x(cPc)−x(lPC))/2
x(HCOO)=A(8.1 ppm)

The composition of the reaction mixture thus determined is subsequently converted to parts by weight and normalized to 100. For conversion of the proportions by weight, the following molar masses (g/mol) are used: cPC and lPC=102, PO and PPO=58, pFA=30 and HCOO=45. The polymer composition is calculated and normalized using the proportions of lPC, PPO and pFA, such that the FIGURE is given here too in parts by weight of 100 (% by weight). The $CO_2$ content of the polymer structure is additionally expressed in % by weight: proportion of lPC·(44/(44+58)), where the factors are each calculated from the molar masses of $CO_2$ (molar mass 44 g/mol) and of propylene oxide (molar mass 58 g/mol) used.

The weight-average and number-average molecular weight of the resulting polymers was determined by means of gel permeation chromatography (GPC). The procedure was based on DIN 55672-1: "Gel permeation chromatography (GPC)—Part 1: Tetrahydrofuran (THF) as elution solvent". Polystyrene samples of known molar mass were used for calibration.

The molar mass of the pFA block in the product polymer was calculated by the following formula:

MW(pFA)=$M_n$(GPC)·(pFA content in the polymer, NMR)/100 where $M_n$(GPC) represents the number average $M_n$ determined by means of GPC. The polydispersity PDI for the molar mass distribution $M_w/M_n$ is reported.

Example 2: Preparation of a Polyoxymethylene-Polyoxyalkylene Carbonate Block Copolymer ($T_{act}$=60° C.)

According to example 1, a polyoxymethylene-polyoxyalkylene carbonate polyol was prepared, except that the temperature in the catalyst activation was set at 60° C. ($T_{act}$). The results are shown in table 1.

Example 3: Preparation of a Polyoxymethylene-Polyoxyalkylene Carbonate Block Copolymer ($T_{act}$=80° C.)

According to example 1, a polyoxymethylene-polyoxyalkylene carbonate polyol was prepared, except that the temperature in the catalyst activation was set at 80° C. ($T_{act}$). The results are shown in table 1.

Example 4: Preparation of a Polyoxymethylene-Polyoxyalkylene Carbonate Block Copolymer ($T_{act}$=100° C.)

According to example 1, a polyoxymethylene-polyoxyalkylene carbonate polyol was prepared, except that the temperature in the catalyst activation was set at 100° C. ($T_{act}$). The results are shown in table 1.

Example 5: Preparation of a Polyoxymethylene-Polyoxyalkylene Carbonate Block Copolymer ($T_{act}$=130° C.) (Comparative Example)

According to example 1, a polyoxymethylene-polyoxyalkylene carbonate polyol was prepared, except that the temperature in the catalyst activation was set at 130° C. ($T_{act}$). The results are shown in table 1.

Example 6: Preparation of a Polyoxymethylene-Polyoxyalkylene Carbonate Block Copolymer ($T_{act}$=150° C.) (Comparative Example)

According to example 1, a polyoxymethylene-polyoxyalkylene carbonate polyol was prepared, except that the temperature in the catalyst activation was set at 150° C. ($T_{act}$). The results are shown in table 1.

Example 7: Preparation of a Polyoxymethylene-Polyoxyalkylene Block Copolymer ($T_{act}$=70° C.)

In a 300 mL pressure reactor with a gas and liquid metering unit, 65 mg of nonactivated DMC catalyst were suspended in 30 g of toluene. The suspension was heated to 130° C. while stirring, $N_2$ was injected to 40 bar and then the $N_2$ pressure was lowered to 15 bar. The injection and release of $N_2$ was conducted twice more in the same way. The suspension thus obtained was cooled down to room temperature and the $N_2$ pressure was released. The pressure reactor was then opened and 15 g of pFA were added to the suspension present. Once the reactor had been closed and heated to 70° C. ($T_{act}$) while stirring (1200 rpm), 15 g of PO were added at a metering rate of 10 g/min. The commencement of the reaction was manifested by a pressure drop to the starting pressure and a slight increase in temperature. On completion of activation, at a temperature of 100° C., 75 g of PO were added continuously at a metering rate of 1 g/min and while stirring (1200 rpm). After the addition of PO had ended, stirring was continued at 100° C. for 2 h (1200 rpm). This was followed by cooling down to room temperature. The reaction mixture was analyzed by means of NMR and GPC analysis. The results are shown in table 1.

Example 8: Preparation of a Polyoxymethylene-Polyoxyalkylene Carbonate Block Copolymer ($T_{act}$=60° C.)

In a 300 mL pressure reactor with a gas and liquid metering unit, 65 mg of nonactivated DMC catalyst were suspended in 30 g of cPC (4-methyl-2-oxo-1,3-dioxolane, cyclic propylene carbonate). The suspension was then heated up to 130° C. and was introduced with 2.5 L/h of nitrogen over the course of 30 min and, at the same time, a reduced pressure of 75-100 mbar was applied. The suspension thus obtained was cooled down to room temperature. The pressure reactor was then opened and 15 g of pFA were added to the suspension present. Once the reactor had been closed and heated to 60° C. ($T_{act}$) while stirring (1200 rpm), 15 g of PO were added at a metering rate of 10 g/min. The commencement of the reaction was manifested by a pressure drop to the starting pressure and a slight increase in temperature. Subsequently, at a temperature of 100° C. and 50 bar of $CO_2$, 75 g of PO were added continuously at a metering rate of 1 g/min and while stirring (1200 rpm). The progress of the reaction was observed by means of $CO_2$ consumption while keeping the pressure in the reactor constant at 50 bar by continuous further metered addition. After the addition of PO had ended, stirring was continued at 100° C. and reaction pressure for 2 h (1200 rpm). This was followed by cooling down to room temperature. The reaction mixture was analyzed by means of NMR and GPC analysis. The results are shown in table 1.

TABLE 1

Results of the polyoxymethylene block copolymer preparation

| No. | $T_{act}$ [° C.] | Residual $PO^a$ content [% by wt.] | $IPC^b$ [% by wt.] | $PPO^b$ [% by wt.] | $pFA^b$ [% by wt.] | $CO_2$ in the polymer [% by wt.] | $M_n$ (GPC) [g/mol] | MW of pFA block [g/mol] | $Formate^a$ [% by wt.] | Methoxy traces | PDI |
|---|---|---|---|---|---|---|---|---|---|---|---|
| 1 | 40 | 1.5 | 50.4 | 30.8 | 18.8 | 21.8 | 3518 | 661 | — | no | 1.98 |
| 2 | 60 | 1.1 | 58.0 | 28.3 | 13.7 | 25.0 | 4733 | 648 | — | no | 2.09 |
| 3 | 80 | 2.5 | 55.3 | 28.9 | 15.9 | 23.8 | 4189 | 660 | — | no | 2.42 |
| 4 | 100 | 2.9 | 57.8 | 28.4 | 13.7 | 24.9 | 4257 | 585 | — | no | 2.45 |
| 5* | 130 | 34.5 | 36.3 | 39.0 | 24.8 | 15.6 | 1200 | 297 | 2.4 | yes | — |
| 6* | 150 | 57.9 | 21.6 | 46.5 | 31.9 | 9.3 | 1020 | 325 | 2.2 | yes | 3.98 |
| 7 | 70 | 0.5 | — | 86.8 | 13.2 | — | 4495 | 593 | — | no | 1.19 |
| 8 | 60 | 0.8 | 49.1 | 33.7 | 17.3 | 21.2 | 3010 | 521 | — | no | 1.52 |

*= comparative example,
$^a$in the reaction mixture,
$^b$in the polymer.

Table 1 summarizes the results for the preparation of the polyoxymethylene block copolymers. By means of the process of the invention, it is possible to obtain products having a defined polyoxymethylene block (pFA block) and a low polydispersity, without observing any breakdown or defragmentation of the paraformaldehyde used as starter compound to smaller oligomers or monomers. In addition, it is possible to obtain, by copolymerization by means of the process of the invention, polyoxymethylene-polyoxyalkylene carbonate block copolymers, wherein virtually complete conversions of the alkylene oxide are achieved with simultaneously high $CO_2$ incorporation rates. Comparative examples 5 and 6 show that there is defragmentation of the polymeric formaldehyde starter and formation of by-products at higher temperatures within the range of activation temperatures typically established for DMC catalysts.

The invention claimed is:

1. A polyoxymethylene block copolymer comprising the catalytic addition product of one or more alkylene oxides and optionally additional comonomers onto at least one polymeric formaldehyde starter compound having at least one terminal hydroxyl group, in the presence of a double metal cyanide (DMC) catalyst, wherein (i) the DMC catalyst is activated in the presence of the polymeric formaldehyde starter compound, in which activation of the DMC catalyst is accomplished by adding a portion, based on the totality of the amount of alkylene oxides used in the activation and polymerization, of one or more alkylene oxides, (ii) one or more alkylene oxides and optionally additional comonomers are added to the mixture from (i), in which the alkylene oxides used in (ii) may be the same as or different than the alkylene oxides used in (i), and (iii) the activation of the DMC catalyst in (i) is effected at an activation temperature ($T_{act}$) of 20 to 120° C.

2. The polyoxymethylene block copolymer as claimed in claim 1, having a polydispersity index of ≤2.5.

3. A polyoxymethylene-polyoxyalkylene carbonate block copolymer comprising an inner polyoxymethylene block or starter and at least one outer polyoxyalkylene carbonate block corresponding to formula (II)

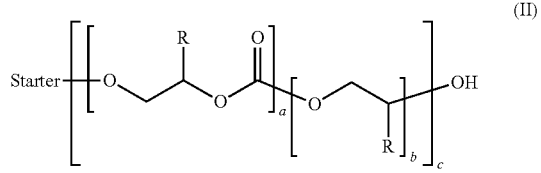
(II)

wherein each R may be the same or different and each represents an organic radical which may be an alkyl, alkylaryl, arylalkyl or aryl radical, each of which may also contain heteroatoms, and a, b and c may be the same or different and each represents an integer, and the structural unit "starter" represents a polyoxymethylene block derived from a polymeric formaldehyde starter compound.

4. A polyurethane polymer obtainable by reacting a di-, tri- and/or polyisocyanate with at least one polyoxymethylene block copolymer as claimed in claim 3.

5. A flexible polyurethane foam or rigid polyurethane foam obtainable by reacting a di-, tri- and/or polyisocyanate with at least one polyoxymethylene block copolymer as claimed in claim 3.

6. An ionic or nonionic surfactant comprising a polyurethane which comprises the reaction product of a di-, tri- and/or polyisocyanate with at least one polyoxymethylene block copolymers as claimed in claim 3.

7. A drilling fluid comprising a polyurethane which comprises the reaction product of a di-, tri- and/or polyisocyanate with at least one of the polyoxymethylene block copolymers as claimed in claim 3.

8. A fuel additive comprising a polyurethane which comprises the reaction product of a di-, tri- and/or polyisocyanate with at least one of the polyoxymethylene block copolymers as claimed in claim 3.

9. A lubricant comprising a polyurethane which comprises the reaction product of a di-, tri- and/or polyisocyanate with at least one of the polyoxymethylene block copolymers as claimed in claim 3.

10. A cosmetic formulation comprising a polyurethane which comprises the reaction product of a di-, tri- and/or polyisocyanate with at least one of the polyoxymethylene block copolymers as claimed in claim 3.

* * * * *